(12) United States Patent
Lindberg et al.

(10) Patent No.: US 10,731,085 B2
(45) Date of Patent: *Aug. 4, 2020

(54) RENEWABLE HYDROCARBON COMPOSITION

(71) Applicant: UPM-KYMMENE CORPORATION, Helsinki (FI)

(72) Inventors: Teemu Lindberg, Lappeenranta (FI); Jaakko Nousiainen, Lappeenranta (FI); Heli Laumola, Helsinki (FI); Arto Rissanen, Lappeenranta (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 0 days.

This patent is subject to a terminal disclaimer.

(21) Appl. No.: 16/195,037

(22) Filed: Nov. 19, 2018

(65) Prior Publication Data

US 2019/0093020 A1    Mar. 28, 2019

Related U.S. Application Data

(63) Continuation of application No. 14/782,139, filed as application No. PCT/EP2014/055630 on Mar. 20, 2014, now Pat. No. 10,150,922.

(30) Foreign Application Priority Data

Apr. 2, 2013  (FI) .................................... 20135309

(51) Int. Cl.
*C10L 1/08*    (2006.01)
*C10G 3/00*    (2006.01)
(Continued)

(52) U.S. Cl.
CPC .................. *C10G 3/50* (2013.01); *C07C 1/22* (2013.01); *C10G 3/45* (2013.01); *C10G 3/46* (2013.01);
(Continued)

(58) Field of Classification Search
CPC .............. C10L 1/08; C10L 2200/0469; C10L 2200/0484
(Continued)

(56) References Cited

U.S. PATENT DOCUMENTS 4,992,605 A    2/1991  Craig et al.
5,180,868 A    1/1993  Baker et al.
(Continued)

FOREIGN PATENT DOCUMENTS

CN    1376191 A    10/2002
EP    1398364 A1    3/2004
(Continued)

OTHER PUBLICATIONS

"Some Petroleum Solvents", 1. Chemical and Physical Data, IARC Monographs, vol. 47, 43-77, published 1987.
(Continued)

*Primary Examiner* — Ellen M McAvoy
(74) *Attorney, Agent, or Firm* — Cantor Colburn LLP

(57) ABSTRACT

The present invention provides a composition comprising 10-40 mass % of $C_{8-30}$ linear alkanes, up to 20 mass % of $C_{7-20}$ aromatic hydrocarbons, at least 90 mass % of which are monoaromatic, and no more than 1 mass % in total of oxygen-containing compounds; wherein the total amount of $C_{8-30}$ alkanes in the composition is 50-95 mass %, and the total amount of $C_{8-30}$ alkanes, $C_{7-20}$ aromatic hydrocarbons and $C_{8-30}$ cycloalkanes is at least 95 mass %; wherein the composition comprises 45-90 mass % in total of $C_{8-30}$ cycloalkanes and $C_{8-30}$ branched alkanes; and wherein the amounts are based on the mass of the composition. Also provided is a method of producing the composition comprising the step of hydroprocessing a biological feedstock using a catalyst and the step of fractionating the product of the hydroprocessing step.

26 Claims, 2 Drawing Sheets

(51) Int. Cl.
| | | |
|---|---|---|
| *C11B 3/00* | (2006.01) | |
| *C10L 1/02* | (2006.01) | |
| *C11C 3/12* | (2006.01) | |
| *C10L 1/04* | (2006.01) | |
| *C07C 1/22* | (2006.01) | |

(52) U.S. Cl.
CPC ............... *C10G 3/48* (2013.01); *C10G 3/49* (2013.01); *C10L 1/026* (2013.01); *C10L 1/04* (2013.01); *C10L 1/08* (2013.01); *C11B 3/00* (2013.01); *C11C 3/12* (2013.01); *C07C 2521/04* (2013.01); *C07C 2523/84* (2013.01); *C07C 2529/072* (2013.01); *C07C 2529/076* (2013.01); *C10G 2300/1014* (2013.01); *C10G 2300/1018* (2013.01); *C10G 2400/04* (2013.01); *C10G 2400/08* (2013.01); *C10L 2200/043* (2013.01); *C10L 2200/0446* (2013.01); *C10L 2200/0469* (2013.01); *C10L 2200/0484* (2013.01); *C10L 2270/026* (2013.01); *C10L 2270/04* (2013.01); *C10L 2290/543* (2013.01); *Y02E 50/13* (2013.01); *Y02P 30/20* (2015.11); *Y02T 50/678* (2013.01)

(58) Field of Classification Search
USPC .......................................................... 585/240
See application file for complete search history.

(56) References Cited

U.S. PATENT DOCUMENTS

| | | | |
|---|---|---|---|
| 5,705,722 | A | 1/1998 | Monnier et al. |
| 5,705,868 | A | 1/1998 | Cox et al. |
| 7,585,337 | B1 | 9/2009 | Turocy |
| 7,691,159 | B2 | 4/2010 | Li |
| 7,897,824 | B2 | 3/2011 | Aulich et al. |
| 8,192,510 | B2 | 6/2012 | Mattingly et al. |
| 8,378,160 | B2 | 2/2013 | Gruber et al. |
| 8,450,541 | B2 | 5/2013 | Seames et al. |
| 8,608,812 | B2 | 12/2013 | Perego et al. |
| 8,697,924 | B2 | 4/2014 | Bauldreay et al. |
| 8,715,371 | B2 | 5/2014 | Behrendt et al. |
| 8,912,374 | B2 | 12/2014 | Van Heuzen et al. |
| 9,005,380 | B2 | 4/2015 | Mathur |
| 9,120,982 | B2 | 9/2015 | Nousiainen et al. |
| 9,181,494 | B2 | 11/2015 | Nousiainen et al. |
| 9,382,483 | B2 | 7/2016 | Knuuttila et al. |
| 9,499,767 | B2 | 11/2016 | Stigsson et al. |
| 9,624,442 | B2 | 4/2017 | Saviainen et al. |
| 10,150,922 | B2 * | 12/2018 | Lindberg ................ C10L 1/026 |
| 2004/0055209 | A1 | 3/2004 | Jakkula et al. |
| 2004/0230085 | A1 | 11/2004 | Jakkula et al. |
| 2007/0204505 | A1 | 9/2007 | Abou-Nemeh |
| 2007/0260102 | A1 | 11/2007 | Duarte Santiago et al. |
| 2009/0250376 | A1 | 10/2009 | Brandvold et al. |
| 2009/0253947 | A1 | 10/2009 | Brandvold et al. |
| 2009/0300970 | A1 * | 12/2009 | Perego .................... C10G 45/60 44/307 |
| 2010/0076236 | A1 | 3/2010 | Van Heuzen et al. |
| 2011/0015459 | A1 | 1/2011 | Aalto et al. |
| 2011/0061290 | A1 | 3/2011 | Aulich et al. |
| 2011/0098494 | A1 | 4/2011 | Weiss et al. |
| 2011/0319683 | A1 | 12/2011 | Abhari et al. |
| 2012/0260565 | A1 | 10/2012 | Nousiainen et al. |
| 2012/0266838 | A1 | 10/2012 | Gosselink et al. |
| 2013/0067801 | A1 | 3/2013 | Nousiainen et al. |
| 2015/0057474 | A1 | 2/2015 | Nousiainen et al. |
| 2015/0159100 | A1 | 6/2015 | Shi et al. |
| 2016/0032204 | A1 | 2/2016 | Nousiainen et al. |

FOREIGN PATENT DOCUMENTS

| | | |
|---|---|---|
| EP | 2097496 B1 | 12/2010 |
| FI | 20125422 | 4/2012 |
| RU | 2160763 C2 | 12/2000 |
| RU | 2397199 C2 | 8/2010 |
| RU | 2441903 C2 | 2/2012 |
| RU | 2456330 C2 | 7/2012 |
| WO | 2006100584 A2 | 9/2006 |
| WO | 2008101945 A1 | 8/2008 |
| WO | 2012069706 A2 | 5/2012 |
| WO | 2012143613 A1 | 10/2012 |
| WO | 201356682 A2 | 10/2013 |

OTHER PUBLICATIONS

Allen et al. (Jan. 11, 2012) Ignition behavior and surrogate modeling of JP-8 and of camelina and tallow hydrotreated renewable jet fuels at low temperatures, Combustion and Flame 160 (2013) 232-239.
ASTM D6729—Apr. 2009, Standard Test Method for Determination of Individual Components in Spark Ignition Engine Fuels by 100 Metre Capillary High Resolution Gas Chromatography; ASTM International; West Conshohockern, PA, 2009; www.astm.org.
ASTM D6729-01, Standard Test Method for Determination of Individual Components in Spark Ignition Engine Fules by 100 Meter Caillary High Resolutuon Gad Chromatography; ASTM International; West Conshohcken, PA, 2001; www.astm.org.
ASTM D6729-04(2009) Standard Test Method for Determination of Individual Components in Spark Ignition Engine Fuels by 100 Metre Capillary High Resolution Gas Chromatography; ASTM International; West Conshohocken, PA, 2009; www.astm.org.
ASTM D6729-04e1, Standard Test Method for Determination of Individual Components in Spark Ignition Engine Fuels by 100 Metre Capillary High Resolution Gas Chromatography; ASTM International; West Conshohocken, PA, 2004; www.astm.org.
Briker et al "Diesel Fuel Analysis by GC-FIMS: Aromatics, n-Paraffins, and Isoparaffins"; Energy & Fuels; 2001; 15; pp. 23-37.
Censullo et al; "Final Report to California Air Resources Board on Contract No. 98-310, Investigation of Low Reactivity Solvents"; Department of Chemistry and Biochemistry California Polytechnic State University; 2002; 1-124.
Chinese Office Action for Chinese Patent Application No. 2014-80020167.2; OA dated Aug. 10, 2016; 15 pages; English Translation.
Chinese Office Action for Chinese Patent Application No. 2014-80020169.1; OA dated Jul. 12, 2016; 25 pages; English Translation.
Chinese Office Action for Chinese Patent Application No. 2014-80020169.1; OA dated Jul. 12, 2016; 7 pages; Non-English Translation.
Common ethanol fuel mixtures; Wikipedia; Mar. 23, 2013.
Corporan et al. (Jul. 17, 2007) Emissions Characteristics of a Turbine Engine and Research Combustor Burning a Fischer-Tropsch Jet Fuel, Energy & Fuels 2007, 21, 2615-2626.
Edwards et al. (Jul. 2012) U.S. Air Force Hydroprocessed Renewable Jet (HRJ) Fuel Research (AFRL-RQ-WP-TR-2013-0108), Interim Report.
Final EA: "Appendix 6A Composition of Crude Oil and Refined Products", Oct. 29, 2008 XP055120506; URL:http://www.epa.gov/region6/6en/xp/longhorn_nepa_documents/ppapp6a.pdf.
Finnish Search Report dated Dec. 18, 2013 re: Application No. 20135309; p. 1; citing: WO 2006100584 A2, WO 2012069706 A2, WO 2013156682 A2 and EP 2097496 B1.
Finnish Search Report dated Dec. 20, 2013 re: Application No. 20135310; p. 1; citing: WO 2013/56682 A2, US 201131983 A1, EP 2097496 B1.
G. Hagenow et al., Handbook of Diesel Engines, Klaus Mollenhauer, Helmut Tschoeke, Springer, 2010 (pp. 80-81).
Gammon "Aviation Fule Quality Control Procedures"; ASTM International; 4th Edition; 2009.
Gasoline Blending Streams Category Test Material Analytical Data; Report of the Petroleum HPV Test Group Consortium Registration # 1100997; Jul. 31, 2008.
Gasoline Blending Streams Category Test Material Analytical Data; Report of the Petroleum HPV Test Group Consortium Registration # 1100997; Jul. 31, 2008; Excerpt of First Pages and Blend F-187.
Goodger et al "Aviation Fuels Technology"; Macmillan 1985.

(56) References Cited

OTHER PUBLICATIONS

Gupta "Gasoline, Diesel abd Ethanol Biofuels from Grasses and Plants"; Cambridge; 2010.
Hancsok et al., Production of bioparaffins by the catalytic hydrogenation of natural triglycerides, Journal of Cleaner Production, vol. 34, 2012, p. 76-81.
Handbook of Aviation Fuel Properties; Coordinating Research Council, Inc.; 1983.
Heather Wansbrough "Tall Oil Production and Processing"; Grant and Hockh's Chemical Dictionary (5th ed); 1987; pp. 1-11; http://nzic.org.nz/ChemProcesses/forestry/4G.pdf.
Hydrocarbon Composition of Gasoline Vapor Emissions from Enclosed Fuel Tanks; Assessment and Standards Division, Office of Transportation and Air Quality and Human Exposure & Atmospheric Sciences Divsion, Office of Research and Development, U.S. Environmental Protection Agency.
International Preliminary Report on Patentability dated Jul. 21, 2015 re: Application No. PCT/EP2014/055828; pp. 1-19.
International Search Report and Written Opinion dated Jun. 13, 2014 re: Application No. PCT/EP2014/055828; pp. 1-13.
International Search Report on Patentability; International Application No. PCT/EP2014/055630; International Filing date Mar. 20, 2014: dated Jul. 7, 2015, 9 pages.
International Search Report; International Application No. PCT/EP2014/055630; International Filing Date Mar. 20, 2014; dated Jun. 25, 2014, 4 pages.
Laurikko et al "High-Concentration Ethanol Fuels for Cold Driving Conditions"; Proceedings of the FISITA 2012 World Automotive Congress, vol. 3: Future Automotive Powertrains (I); Nov. 2012.
Lee et al "Handbook of Alternative Fuel Technologies"; CRC Press 2007.
Material Safety Data Sheet; ETHYK Tertiary Butyl Ether, Octane Enhancer; Jul. 29, 2004; pp. 1-17.
McSweeney et al "Tall Oil and Its Uses II"; Pulp Chemicals Asociation, Inc.; pp. 13-19.
O. Hutzinger; "Fuel Oxygenates"; The Handbook of Environmental Chemistry, vol. 5 Water Pollution Part R.
Robinson et al "Hydrotreating and Hydrocracking: Fundamentals";ResearchGate; Chapter—Oct. 2007; DOI:10.1007/978-0-387-25789-1_7; https://www.researchgate.net/publication/227247349.
Safety Data Sheet for Tesoro Gasoline, Unleaded; Aug. 9, 2012.

Simacek et al., Hydrocracking of petroleum vacuum distillate containing rapeseed oil: Evaluation of diesel fuel, Fuel 89 (2010) 1508-1513.
Speight "Handbook of Petroleum Product Analysis"; John Wiley & Sons; 2002.
The Engineering Toolbox "Hydrocarbons, linear alcohols and acids-density: Density of differenct types of hydrocarbons, alcohols and acids as function of carbon number, at 20° C./68°"; www.EngineeringToolBox.com.
Toxicologic Assessment of Jet-Propulsion Fuel 8; Natinal Research Council of the National Academies; National Academic Press 2003.
Toxicological Profile for Gasoline; U.S. Department of Health and Human Services; Jun. 1995.
Toxicological Profile for Gasoline; U.S. Department of Health and Human Services; Jun. 1995; Excerpt of pp. 107-111.
Written Opinion of the International Searching Authority; International Application No. PCT/EP2014/055630; International Filing Date Mar. 20, 2014, dated Jun. 25, 2014, 9 pages.
Y. Bricker et al. "Diesel Fuel Analysis by GC-FIMS: Aromatics, n-Paraffins, and Isoparaffins", Energy & Fuels, American Chemical Society, Jan. 17, 2001, vol. 15, No. 1, pp. 23-37, XP055077679.
Feng, Yi et al., "Chemical Composition of Tall Oil-Based Cetane Enhancer for Diesel Fuels" First Biomass Conference of the Americas: Energy, Environment, Agriculture, and Industry, vol. II, Aug. 1993.
France, Colin, "Products from Oil" Oct. 19, 2007, retrieved from Internet on Sep. 9, 2019 from: https://web.archive.org/web/20071019040049/http://www.gcsescience.com/o5.htm.
Hendricks, Robert C. et al., "Aviation Fueling: A Cleaner, Greener Approach", International Journal of Rotating Machinery, vol. 2011, No. 782969, Aug. 2011 (13 pages).
Kirkinen, Johanna et al., "Greenhouse Impact Assessment of Peat-based Fischer-Tropsch Diesel Life-Cycle" Energy Policy, vol. 38, Oct. 21, 2009 (Abstract Only).
Soveran, Doug et al., "The Effect on Diesel Engine Emissions With High Cetane Additives From Biomass Oils", Jan. 1, 1992, in Proceedings, American Chemical Society of fuel (Division of fuel chemistry) meeting, San Francisco, CA, pp. 74-85.
Stumborg, Mark et al., "Hydroprocessed Vegetable Oils for Diesel Fuel Improvement", Bioresource Technology 56, 1996, pp. 13-18.
The Engineering Toolbox, (2017) "Hydrocarbons, alcohols and acids—boiling points", downloaded from internet Sep. 18, 2019 from: https://www.EngineeringToolBox.com/melting-boiling-temperature-hydrocarbons-alkane-alkene-benzen-aromatic-alcohol-acid-naphthalene-d_1940.html (10 pages).

* cited by examiner

RENEWABLE HYDROCARBON COMPOSITION

CROSS-REFERENCE TO RELATED APPLICATION

This application is a continuation of U.S. application Ser. No. 14/782,139 filed on Oct. 2, 2015, which is an U.S. national stage of application No. PCT/EP2014/055630, filed on 20 Mar. 2014 and claims priority to Finish application no. 20135309 filed on 2 Apr. 2013. The disclosures of all of these applications is incorporated herein by reference in its entirety.

TECHNICAL FIELD

The present invention relates to a hydrocarbon composition. More particularly, the present invention relates to a composition which contains a variety of hydrocarbons and is obtainable from a renewable biological feedstock. The composition can be used as a fuel component.

BACKGROUND OF THE INVENTION

Conventional diesel fuel produced from crude oil ("petrodiesel") contains a complex mixture of hydrocarbons which typically have 10-22 carbon atoms. These hydrocarbons include linear and branched alkanes, cycloalkanes and aromatic hydrocarbons. As a consequence of the crude oil source and the production process (particularly fractional distillation), petrodiesel typically contains up to 40 mass % of aromatic hydrocarbons, more usually 25-35 mass % of aromatic hydrocarbons. A significant proportion, usually in the order of 15-20 mass %, of the aromatic hydrocarbons are polycyclic (i.e. contain two or more aromatic rings). Such compounds are harmful to health (e.g. carcinogenic) and have poor combustion properties.

In most countries, diesel fuel must satisfy certain regulatory requirements before it can be sold. In the European Union, diesel fuels must comply with the EN 590 Standard. This requires diesel fuels to have various physical and chemical properties, including a density of 820-845 kg/m$^3$ at 15° C. (as measured using test method EN ISO 3675 or EN ISO 12185), a maximum polycyclic aromatic hydrocarbon content of 11 mass %, and a cetane number of at least 51.0 (as measured using test method EN ISO 5165).

Renewable fuels derived from biological matter ("biofuels") are gaining popularity as a more environmentally friendly alternative to conventional fossil fuels. Examples of biofuels include biodiesel, which is typically produced by transesterification of triglycerides contained in vegetable oils (e.g. soybean oil). This yields a mixture of fatty acid alkyl esters (e.g. fatty acid methyl ester (FAME)). Biodiesel can also be produced from animal fats (e.g. tallow).

FAME produced from a biological feedstock can be blended with petrodiesel, but in an amount of no more than 7 vol. % according to EN 590. This is due to the chemical and physical differences between FAME and petrodiesel. FAME contains ester groups, which are largely absent from petrodiesel. This difference is responsible for the inferior properties of FAME biodiesel at low temperatures and the inferior storage stability of FAME biodiesel. FAME biodiesel also has a tendency to degrade natural rubber components of automobiles (e.g. rubber gaskets).

FAME biodiesel has a significantly lower mass-based energy content than petrodiesel; the energy content of FAME biodiesel is typically about 38 MJ/kg, whereas the energy content of petrodiesel is typically about 43 MJ/kg. Taking into account the higher density of FAME biodiesel (approximately 885 kg/m$^3$), the volume-based energy contents of FAME biodiesel and petrodiesel are typically about 34 MJ/l and 36 MJ/l respectively.

A further disadvantage of FAME biodiesel is that its manufacture by transesterification of triglycerides produces a large quantity of glycerol. This is often an unwanted by-product due to low market demand. Moreover, purification of the crude glycerol is energy intensive.

A type of second generation biofuel is "biomass-to-liquid" (BTL) biofuel, which is produced from gasified biomass using the Fischer-Tropsch process. The gasified carbonaceous material reacts to produce a syngas (a mixture of carbon monoxide and hydrogen), which in turn undergoes polymerisation to produce hydrocarbons.

BTL biodiesel typically has a density of about 780 kg/m$^3$, which is significantly lower than the density of petrodiesel. This means that the volume-based energy content of BTL biodiesel is only about 95% of that of petrodiesel.

An object of the present invention is to provide a renewable hydrocarbon composition which can be used as a fuel component.

SUMMARY OF THE INVENTION

A first embodiment of the present invention is a composition comprising 10-40 mass % of $C_{8-30}$ linear alkanes, up to 20 mass % of $C_{7-20}$ aromatic hydrocarbons, at least 90 mass % of which are monoaromatic, and no more than 1 mass % in total of oxygen-containing compounds; wherein the total amount of $C_{8-30}$ alkanes in the composition is 50-95 mass %, and the total amount of $C_{8-30}$ alkanes, $C_{7-20}$ aromatic hydrocarbons and $C_{8-30}$ cycloalkanes is at least 95 mass %; and wherein the amounts are based on the mass of the composition.

The above composition has a high content of hydrocarbons and a low content of oxygen-containing compounds (oxygenates). The total hydrocarbon content is comparable to that of petrofuels. This makes the composition highly suitable for use as a petrofuel replacement or a biofuel component to be blended with a petrofuel. The composition is particularly suited to being blended with petrodiesel or kerosene.

Unlike first generation biodiesels produced by transesterification, the composition of the present invention contains no ester compounds or a negligible amount of ester compounds. Accordingly, the composition does not suffer from the poor low-temperature properties and poor storage stability of first generation biodiesels, and there is no risk of the composition degrading automobile components in the manner of first generation biodiesel. Also, the distillation curve of the composition of the invention is closer to that of petrodiesel than first generation biodiesels and does not suffer from the disadvantages of high boiling point compounds. Such compounds worsen the combustion properties of diesel fuels.

A key feature of the composition of the invention is that it can be produced from a renewable biological feedstock. More particularly, it is possible to produce the composition by subjecting a biological feedstock (e.g. crude tall oil) to hydroprocessing (i.e. treatment with hydrogen gas) using a catalyst. Hydroprocessing chemically alters compounds in the feedstock; heteroatoms (e.g. sulfur and oxygen) can be removed from feedstock compounds and unsaturated compounds can be hydrogenated.

As compared to conventional petrodiesel, the composition of the invention has a low content of polycyclic aromatic hydrocarbons (no more than 2 mass % of $C_{7-20}$ polycyclic aromatics). Also, the amount of monoaromatic hydrocarbons relative to the total amount of aromatic hydrocarbons is higher for the present composition than for petrodiesel. The composition is thus useful for reducing the polyaromatic hydrocarbon content of a fuel and increasing the proportion of monoaromatic hydrocarbons. This is beneficial in terms of enhancing combustion and decreasing soot emissions.

A further advantage of the present composition over known biofuels is that, due to the amounts of the various hydrocarbons, the density and mass-based energy content of the composition are such that its volume-based energy content is similar to that of petrodiesel.

Another embodiment of the invention is a method for producing a composition as defined above, the method comprising the steps of hydroprocessing a biological feedstock using one or more catalysts and fractionating the product of the hydroprocessing step. As mentioned above, the ability to produce the composition of the invention from a biological feedstock enables the composition to be used as a renewable fuel component.

A further embodiment of the invention is the use of a composition as defined above as a fuel or a fuel component. The composition is suitable for use as a biofuel on its own or as a renewable component of a fuel (e.g. diesel) due to its high hydrocarbon content and low oxygen content.

A still further embodiment of the invention is a fuel blend comprising a composition as defined above. As already mentioned, the composition is compatible with petrofuels, particularly petroleum-derived diesel and kerosene. A diesel blend can easily be made compliant with the EN 590 Standard.

DETAILED DESCRIPTION

Figure 1:
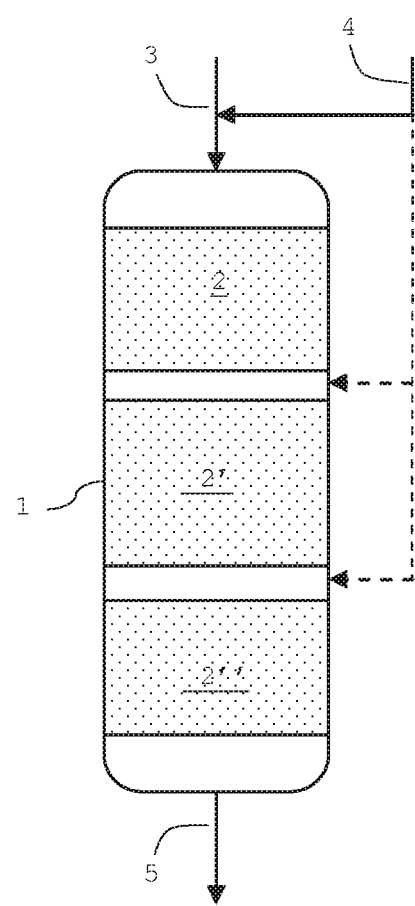
FIG. 1: Schematic diagram illustrating a hydroprocessing reactor suitable for use in the method of the present invention.

In this application, the terms "comprising", "comprise(d)", "containing" and "contain(ed)" in the context of one or more components of a composition cover the case where the named components are the sole components of the composition as well as the case where other components are present. When a composition is defined as containing a compound defined in generic terms (e.g. $C_{8-30}$ linear alkanes) in a certain amount, the definition of the same amount of a subset of compounds (e.g. $C_{9-23}$ linear alkanes) or a specific compound (e.g. heptadecane) falling within the generic class means that the subset of compounds or the specific compound is present in said amount and other compounds (e.g. $C_8$ linear alkanes) within the generic class may or may not be contained in the composition.

The composition of the invention is described in detail below. Unless otherwise specified, all amounts are in mass % based on the mass of the composition.

The composition comprises 10-40 mass % of $C_{8-30}$ linear alkanes. The content of $C_{8-30}$ linear alkanes is preferably 20-40 mass %, more preferably 20-30 mass % and most preferably 20-25 mass %. The linear alkanes are preferably $C_{9-23}$ linear alkanes, more preferably $C_{9-20}$ linear alkanes, still more preferably $C_{12-18}$ linear alkanes, and most preferably $C_{15-18}$ linear alkanes.

In one embodiment, the composition contains 20-40 mass % of $C_{9-23}$ linear alkanes. In another embodiment, the composition contains 20-40 mass % of $C_{9-20}$ linear alkanes. In a further embodiment, the composition contains 20-40 mass % of $C_{12-18}$ linear alkanes. In a further embodiment, the composition contains 20-40 mass % of $C_{15-18}$ linear alkanes. In a further embodiment, the composition contains 20-30 mass % of $C_{9-23}$ linear alkanes. In a further embodiment, the composition contains 20-30 mass % of $C_{9-20}$ linear alkanes. In a further embodiment, the composition contains 20-30 mass % of $C_{12-18}$ linear alkanes. In a further embodiment, the composition contains 20-30 mass % of $C_{15-18}$ linear alkanes.

The composition comprises up to 20 mass % of $C_{7-20}$ aromatic hydrocarbons. The content of $C_{7-20}$ aromatic hydrocarbons is preferably 0.1-15 mass %, more preferably 0.5-12 mass %, still more preferably 1-10 mass % and most preferably 5-10 mass %, higher amounts being particularly suitable for aviation fuels. The aromatic hydrocarbons are preferably $C_{8-19}$ aromatic hydrocarbons, more preferably $C_{9-15}$ aromatic hydrocarbons and most preferably $C_{9-12}$ aromatic hydrocarbons. The carbon numbers denote the total number of carbon atoms contained in the aromatic hydrocarbons, including the carbon atoms contained in non-aromatic constituents (e.g. alkyl substituents of an aromatic ring). Examples of the aromatic hydrocarbons include ethylbenzene, xylenes, butyl benzene, ethyl butyl benzene and hexyl benzene.

In one embodiment, the composition contains 0.1-15 mass % of $C_{8-19}$ aromatic hydrocarbons. In another embodiment, the composition contains 0.1-15 mass % of $C_{9-15}$ aromatic hydrocarbons. In a further embodiment, the composition contains 0.5-12 mass % of $C_{8-19}$ aromatic hydrocarbons. In a further embodiment, the composition contains 0.5-12 mass % of $C_{9-15}$ aromatic hydrocarbons. In a further embodiment, the composition contains 1-10 mass % of $C_{8-19}$ aromatic hydrocarbons. In a further embodiment, the composition contains 1-10 mass % of $C_{9-15}$ aromatic hydrocarbons.

At least 90 mass % of the $C_{7-20}$ aromatic hydrocarbons contained in the composition are monoaromatic hydrocarbons (hydrocarbons containing a single aromatic ring). This means that the composition contains a maximum of 2 mass % of $C_{7-20}$ polyaromatic hydrocarbons (hydrocarbons containing two or more aromatic rings). The content of polyaromatic hydrocarbons is preferably no more than 1 mass %, more preferably no more than 0.5 mass %, still more preferably no more than 0.2 mass % and most preferably no more than 0.1 mass %. As mentioned above, the reduced content of polyaromatic hydrocarbons relative to conventional petrodiesel is advantageous in terms of reducing soot emissions during combustion and reducing the health hazard posed by the composition.

The total amount of $C_{8-30}$ alkanes in the composition is 50-95 mass %, preferably 60-95 mass %, more preferably 60-90 mass %, still more preferably 70-90 mass % and most preferably 70-85 mass %. Accordingly, the composition contains 10-85 mass % of $C_{8-30}$ branched alkanes according to the broadest embodiment of the invention. An increased amount of branched alkanes improves the cold flow properties of the composition. In a particular embodiment, the composition contains 20-85 mass %, 30-85 mass %, 60-85 mass %, 50-70 mass %, 20-60 mass %, 40-60 mass %, 30-60 mass %, 20-50 mass %, 30-50 mass % or 20-40 mass % of $C_{8-30}$ branched alkanes, preferably 40-60 mass % of $C_{8-30}$ branched alkanes. The branched alkanes are preferably $C_{9-23}$ branched alkanes, more preferably $C_{9-20}$ branched alkanes, still more preferably $C_{12-18}$ branched alkanes and most preferably $C_{5-18}$ branched alkanes. Such branched alkanes may be present in any of the aforementioned amounts (e.g. 40-60 mass % of $C_{9-23}$ branched alkanes).

A reference to alkanes of an unspecified type (e.g. $C_{8-30}$ alkanes) covers both linear and branched alkanes, but not cycloalkanes.

The composition preferably comprises 40-90 mass % in total of $C_{8-30}$ cycloalkanes and $C_{8-30}$ branched alkanes, more preferably 45-90 mass %, still more preferably 45-80 mass % and most preferably 60-80 mass % of $C_{8-30}$ cycloalkanes and $C_{8-30}$ branched alkanes. On an individual level, the composition preferably comprises 10-40 mass % of $C_{8-30}$ cycloalkanes, more preferably 10-30 mass % of $C_{8-30}$ cycloalkanes and most preferably 15-25 mass % of $C_{8-30}$ cycloalkanes. The cycloalkanes are preferably $C_{8-19}$ cycloalkanes, more preferably $C_{8-14}$ cycloalkanes.

The composition contains $C_{8-30}$ alkanes, $C_{7-20}$ aromatic hydrocarbons and $C_{8-30}$ cycloalkanes in a total amount of at least 95 mass %. Accordingly, the composition contains no more than 5 mass % of other hydrocarbons, including alkenes. Such a low alkene content is beneficial in terms of the oxidation stability of the composition.

It is preferred that the composition contains no more than 2 mass % of alkenes, more preferably no more than 1 mass % and most preferably no more than 0.5 mass % of alkenes. Such low alkene contents can be achieved using the hydroprocessing method of the invention.

The composition contains no more than 1 mass % in total of oxygen-containing compounds (oxygenates). This ensures that the composition has favourable low-temperature properties, is stable during storage and is compatible with petroleum-derived fuels, particularly diesel and kerosene. The total amount of oxygenates (e.g. esters) contained in the composition is preferably no more than 0.5 mass %, more preferably no more than 0.2 mass % and still more preferably no more than 0.1 mass %. In elemental terms, it is preferred that the composition contains no more than 0.1 mass % of oxygen, more preferably no more than 0.05 mass % of oxygen and most preferably no more than 0.02 mass % of oxygen.

The composition can have a density comparable to that of petrodiesel. In one embodiment, the composition has a density of 795-830 kg/m³, as measured at 15° C. by the method of the EN ISO 12185 Standard. Thus, the density of the composition may be lower than or fall within the range specified in the EN 590 Standard.

It is preferred that the composition has a lower heating value of 42.0-45.5 MJ/kg, as measured by the method of the DIN 51900 Standard. This is comparable to or higher than the lower heating value of petrodiesel. A higher value can compensate for a reduced density relative to petrodiesel.

In one embodiment, the composition has a cetane number of at least 55, as measured using the method of the EN ISO 5165 Standard. This range falls well above the lower limit of 51 specified in the EN 590 Standard. The cetane number of the composition is preferably at least 56, more preferably at least 57, still more preferably at least 60, even more preferably at least 63 and most preferably at least 65. In comparison, conventional petrodiesel typically has a cetane number of approximately 53. The composition of the invention can thus have utility as a cetane number-increasing agent, thereby improving the ignition properties of a diesel fuel.

The composition can be made to have similar distillation properties to conventional diesel or kerosene. In one embodiment, the composition begins to distil at a temperature of at least 150° C., at least 160° C. or at least 170° C. Distillation may be completed at 350° C. or less, 345° C. or less or 340° C. or less. It is preferable that at least 95 vol. % of the composition is distilled at temperatures up to 360° C. EN 590 specifies a minimum distillate quantity of 85 vol. % at 350° C. for diesel fuels (test method EN ISO 3405).

In the case that the composition is intended for use as an aviation fuel component, it is preferred that the composition has a final boiling point in the range of 200-280° C.

As a further property, the mean-average molecular weight of the composition can be as low as 160 g/mol. In one embodiment, the average molecular weight is 160-180 g/mol or 170-180 g/mol. In another embodiment, the average molecular weight is 220-230 g/mol.

The method for producing the composition of the invention is explained in detail below.

The method comprises the step of hydroprocessing a biological feedstock using one or more catalysts. Hydroprocessing chemically alters compounds contained in the feedstock. Typical reactions include hydrogenation of double bonds, deoxygenation (e.g. by decarboxylation), desulfurisation, denitrification, isomerisation, ring-opening, aromatisation, dearomatisation and cracking. For instance, any terpenes contained in the feedstock can be converted to non-terpenic acyclic and/or cyclic hydrocarbons (e.g. 1-isopropyl-4-methylcyclohexane and 2,6-dimethyloctane) by hydrogenation of olefinic bonds and ring-opening. Aromatic hydrocarbons (e.g. 1,1,2,5-tetramethylbenzene, 1,1,2,3-tetramethylbenzene and 1-isopropyl-4-methylbenzene) can be produced by dehydrogenation of cyclohexane-containing compounds derived from terpenes. Bound contaminants such as sulfur can be converted to gaseous compounds (e.g. hydrogen sulfide), which can be removed in a subsequent step.

The biological feedstock can be selected from a range of feedstocks. Particular examples are the following:
i) plant (vegetable) and animal (including fish) fats, oils and waxes;
ii) free fatty acids obtained by hydrolysis or pyrolysis of plant and animal fats, oils and waxes;
iii) fatty acid esters obtained by transesterification of plant and animal fats, oils and waxes;
iv) metal salts of fatty acids obtained by saponification of plant and animal fats, oils and waxes;
v) anhydrides of fatty acids obtained from plant and animal fats, oils and waxes;
vi) esters obtained by esterification of free fatty acids of plant and animal origin with alcohols;
vii) fatty alcohols or aldehydes obtained as reduction products of fatty acids from plant and animal fats, oils and waxes;
viii) recycled food-grade fats and oils;
ix) fats, oils and waxes obtained by genetic engineering;
x) dicarboxylic acids, polyols (including diols), hydroxyketones, hydroxyaldehydes, hydroxycarboxylic acids and corresponding di- and multifunctional sulfur- and nitrogen-containing compounds;
xi) compounds derived from algae; and
xii) mixtures of any of the above.

In one embodiment, the feedstock comprises or consists of one or more of tall oil, tall oil components (e.g. tall oil fatty acids and tall oil resin acids) and tall oil derivatives (e.g. distilled tall oil, tall oil heads and tall oil pitch). Tall oil is obtained from kraft pulping of wood, especially coniferous wood. In general, tall oil contains saturated and unsaturated oxygen-containing organic compounds such as resin acids (mainly abietic acid and its isomers), fatty acids (mainly linoleic acid, oleic acid and linolenic acid), unsaponifiables, fatty alcohols, sterols and other alkyl hydrocarbon derivatives, as well as minor amounts of inorganic impurities (e.g. alkaline metal compounds, sulfur, silicon, phosphorus, calcium and iron compounds). Tall oil usually does not contain a significant amount of triglycerides since these compounds are decomposed during the pulping process. "Tall oil" covers soap oil as well as crude tall oil.

In a preferred embodiment, the feedstock comprises at least 15 mass %, more suitably at least 25 mass %, at least 35 mass % or at least 45 mass %, of $C_{12-18}$ fatty acids (e.g. linoleic acid, oleic acid and linolenic acid); at least 5 mass %, more suitably at least 15 mass %, at least 20 mass % or at least 25 mass %, of resin acids (e.g. abietic acid, pimaric acid and isomers thereof); and at least 10 mass %, more suitably at least 15 mass % or at least 20 mass %, of neutral products (e.g. sterols) based on the mass of the feedstock. This feedstock is suitably tall oil.

Hydroprocessing is performed using one or more catalysts, which can be catalysts conventionally employed for this process. Effective catalysts comprise one or more metals selected from Group VIA and Group VIII metals, particularly useful examples of which are Mo, W, Co, Ni, Pt and Pd. The catalyst(s) can also contain one or more support materials, examples of which are zeolite, alumina ($Al_2O_3$), zeolite-alumina, alumina-silica ($SiO_2$), alumina-silica-zeolite and activated carbon.

The method suitably utilises a hydrodeoxygenation (HDO) catalyst, which is intended for removal of oxygen but is also capable of removing other heteroatoms such as sulfur and nitrogen from organic compounds as well as catalysing hydrogenation of unsaturated bonds. Effective HDO catalysts include those containing a mixture of CoO and $MoO_3$ ("CoMo") and/or a mixture of NiO and $MoO_3$ ("NiMo"), and one or more support materials selected zeolite, alumina, zeolite-alumina, alumina-silica, alumina-silica-zeolite and activated carbon. A mixture of NiO and $MoO_3$ on an alumina support is particularly effective.

Another effective hydroprocessing catalyst is a multifunctional catalyst. This type of catalyst is capable of catalysing the same reactions as HDO catalysts. In addition, multifunctional catalysts can effect isomerisation (e.g. conversion of linear alkanes to branched alkanes) and cracking, which decreases the hydrocarbon chain length. Both isomerisation and cracking can improve cold flow properties.

Useful multifunctional catalysts include those containing NiW and one or more support materials selected from zeolite, alumina, zeolite-alumina, alumina-silica, alumina-silica-zeolite and activated carbon. An alumina support with adequate acidic properties is preferred. The acidity can be adjusted by adding zeolites to the support. For example, the support comprises zeolite-alumina or alumina-silica-zeolite.

A further suitable hydroprocessing catalyst is a hydroisomerisation (HI) catalyst. HI catalysts are capable of causing isomerisation reactions. Example catalysts contain a Group VIII metal (e.g. Pt, Pd, Ni) and/or a molecular sieve. Preferred molecular sieves are zeolites (e.g. ZSM-22 and ZSM-23) and silicoaluminophosphates (e.g. SAPO-11 and SAPO-41). HI catalysts may also contain one or more of the support materials described above. In one embodiment, the HI catalyst comprises Pt, a zeolite and/or silicoaluminophosphate molecular sieve, and alumina. The support may alternatively or additionally contain silica.

According to a preferred embodiment, the hydroprocessing step is performed using one or both of the following catalysts (i) and (ii), and optionally the following catalyst (iii):

(i) a catalyst comprising $MoO_3$, one or both of CoO and NiO, and one or more support materials;
(ii) a catalyst comprising NiW and one or more support materials;
(iii) a catalyst comprising a Group VIII metal and/or a molecular sieve;

wherein the support materials are selected from zeolite, alumina, zeolite-alumina, alumina-silica, alumina-silica-zeolite and activated carbon.

Suitable catalyst combinations are (i) and (ii); (i) and (iii); (ii) and (iii); and (i), (ii) and (iii). It is, however, also possible for the hydroprocessing step to be carried out using catalyst (i) alone or catalyst (ii) alone.

It is preferable to remove sulfur compounds from the feedstock before it is reacted with catalyst (iii) in the case that catalyst (iii) contains a Group VIII metal (e.g. Pt). This prevents poisoning of catalyst (iii) by sulfur compounds. Preferably, the feedstock is contacted with catalyst (i) prior to catalyst (iii).

Hydroprocessing is performed using one reactor or using two or more reactors (i.e. separate pressure vessels). In the case that a plurality of hydroprocessing reactors are employed, the reactors can be connected in series so that the product of one reactor is fed to another reactor. Each reactor can contain a single "bed" comprising one or more catalysts and optionally other materials such as an inert material (e.g. for temperature control). Alternatively, any given reactor may contain a plurality of catalyst beds which each contain one or more catalysts and optionally other materials such as an inert material. Examples of the inert material include alumina, silicon carbide and glass beads. Reactors containing more than one catalyst bed can comprise a quench gas inlet and a distributer between any two catalyst beds.

Catalyst beds can be monolayered (e.g. contain one catalyst or a mixture of catalysts) or comprise a plurality of layers containing different proportions of two or more catalysts. The layers can vary in size.

Inert material-containing layers can be used to separate catalyst beds. Moreover, an inert layer may be inserted before the first catalyst bed and/or after the final catalyst bed. Inert layers can be used to capture certain substances and provide an even distribution of the feedstock/reaction mixture. An inert layer located upstream of the first catalyst bed may also be used to preheat the feedstock.

Inert layers can also contain active catalyst material having the function of removing harmful components (e.g. metals) from the feedstock/reaction mixture.

Hydroprocessing can be performed using a reactor containing a single catalyst such as catalyst (i). This catalyst can be contained in a single bed or in multiple beds in the reactor.

In an embodiment, hydroprocessing is performed using one or more reactors which each contain catalyst (i) and one or both of catalysts (ii) and (iii). In this case, catalyst (i) and catalyst (ii) and/or (iii) may be contained in the same bed (e.g. in a reactor having a single catalyst bed), separate beds or a mixture thereof in any given reactor. Preferably, at least one reactor contains catalyst (i) as well as catalyst (ii) and/or catalyst (iii), and the total amount of catalysts (ii) and (iii) relative to the total amount of catalysts (i), (ii) and (iii) increases continuously in the direction of flow of the biological feedstock in the reactor. This may occur over a single catalyst bed containing all of the catalysts (in layered or mixed form) or over a plurality of catalyst beds (e.g. two beds) which each contain one or all catalysts. The exact proportions of the catalysts can be varied according to the nature of the feedstock. Increased amounts of catalysts (ii) and (iii) can be used to increase the levels of cracking and isomerisation.

In one particular example, a hydroprocessing reactor contains two or three catalyst beds and the proportion of catalyst (ii) and/or catalyst (iii) increases on moving between the catalyst beds in the flow direction. The first bed contains only catalyst (i) or a mixture of catalyst (i) and catalyst (ii) in a particular mass ratio (e.g. 70-99:1-30), the second bed contains a mixture of catalyst (i) and one or both of catalysts (ii) and (iii) in a lower mass ratio (e.g. 30-70:30-70 (total of (ii) and (iii)), and the third bed (when present) contains a mixture of catalyst (i) and one or both of catalysts (ii) and (iii) in a still lower mass ratio (e.g. 2-15:85-98) or contains only catalyst (ii) and/or catalyst (iii).

In another embodiment, a reactor contains two catalyst beds only, the first bed (closest to the feedstock inlet) containing catalyst (i) and no catalyst (ii) or catalyst (iii), and the second bed containing catalyst (ii) and/or catalyst (iii) but no catalyst (i).

In an alternative preferred embodiment, the relative amounts of the catalysts vary across two or more interconnected reactors. For instance, a first reactor contains a catalyst bed comprising only catalyst (i) or a mixture of catalyst (i) and catalyst (ii) in a particular mass ratio (e.g. 70-95:5-30), and a second reactor connected downstream of the first reactor contains a catalyst bed comprising a mixture of catalyst (i) and one or both of catalysts (ii) and (iii) in a lower mass ratio (e.g. 2-15:85-98 (total of (ii) and (iii)) or comprising only catalyst (ii) and/or catalyst (iii).

It is preferred that hydroprocessing reactors are connected such that no components of the reaction mixture exiting a first reactor (e.g. a reactor containing catalyst (i)) are removed before passing the mixture to the next reactor (e.g. a reactor containing catalyst (ii)). In this way, there is a single, closed (other than the reactor inlets and outlets) hydroprocessing system divided across more than one reactor. Similarly, it is preferred that the product having passed through one or more guard beds (see below) passes to the hydroprocessing bed(s) without the removal of by-products or other components. In general, all catalyst beds are preferably connected in this manner.

FIG. 1 illustrates a hydroprocessing reactor suitable for use in the process of the present invention. The hydroprocessing reactor 1 contains three catalyst beds (beds 2, 2' and 2"), which are optionally separated by quench gas distributers. Catalyst bed 2 is located closest to the biological feedstock inlet, and catalyst bed 2" is located closest to the outlet, which is connected to line 5. At least bed 2 contains catalyst (i) (e.g. NiMo/Al$_2$O$_3$), at least bed 2" contains catalyst (ii) (e.g. NiW/zeolite/Al$_2$O$_3$), and at least one bed contains catalyst (i) in combination with catalyst (ii). For instance, beds 2 and 2' both contain catalysts (i) and (ii), the proportion of catalyst (ii) in bed 2' being higher than that in bed 2. Suitable content ratios are 70-99 (catalyst (i)): 1-30 mass % (catalyst (ii)) and 30-70: 30-70 mass % for beds 2 and 2' respectively. The proportion of catalyst (ii) in bed 2" is higher still (e.g. 85-100 mass %), preferably 100 mass %.

Line 3 supplies the feedstock to the reactor 1, whilst line 4 supplies pure hydrogen or a hydrogen-containing gas to the reactor 1. The hydrogen line 4 connects to the feed line 3 shortly before the feed line enters the reactor 1, thereby allowing pre-mixing of the feedstock and hydrogen. In an alternative embodiment, lines 3 and 4 are connected separately to the reactor 1.

The hydrogen supply line optionally splits to form one or more branch lines which are connected to the reactor 1 downstream of the feedstock inlet. In FIG. 1, optional quench gas lines are connected between the catalyst beds to allow for control of the hydrogen content of the catalyst beds and control of the reactor temperature.

HDO and multifunctional catalysts (catalysts (i) and (ii)) may benefit from the addition of sulfur before the feedstock is introduced into the reactor. A suitable sulfiding agent is dimethyl disulfide. On the other hand, the performance of an HI catalyst (catalyst (iii)) may be enhanced by preventing sulfur coming into contact with the catalyst. Accordingly, as mentioned above, if a hydroprocessing reactor contains an HI catalyst, means for preventing sulfur from contacting the HI catalyst are preferably provided. Sulfur can be removed from the reactor downstream of an HDO/multifunctional catalyst but upstream of an HI catalyst.

A suitable reactor temperature during hydroprocessing is 280-450° C., preferably 350-420° C. and most preferably 350-390° C. A suitable reactor pressure is 10-250 bar, preferably 30-130 bar and most preferably 80-110 bar.

The products of hydroprocessing are influenced by the feed rate of the feedstock. The weight hourly spatial velocity (WHSV) of the feedstock can be 0.1-5.0 h$^{-1}$, preferably 0.2-0.8 h$^{-1}$ and most preferably 0.3-0.7 h$^{-1}$. WHSV is defined as follows:

$$WHSV = V/m$$

wherein "V" is the feed velocity of the feedstock (g/h) and "m" is the mass of the catalyst (g).

The ratio of the amount of hydrogen supplied to the hydroprocessing reactor(s) to the amount of feedstock supplied to the reactor(s) also has a bearing on the reaction. It is preferred that this ratio is 600-4000 Nl/l (Nl=normal litre), more preferably 1300-2200 Nl/l.

The amount of monoaromatic hydrocarbons can be controlled by appropriate selection of hydroprocessing conditions. For instance, the amount of monoaromatics can be increased by increasing the hydroprocessing reactor temperature. Lowering the reactor pressure also causes an increase in the monoaromatics content.

The process of the invention can include additional steps before and/or after the hydroprocessing step. Such optional steps include purification of the feedstock and purification of the product of hydroprocessing prior to fractionation.

The feedstock may be purified by evaporation. This may be accomplished in one or more stages. In the case that two or more evaporators are employed, the temperature is typically increased successively from the first to the second and subsequent evaporators. In one embodiment, the feedstock is heated to 110-230° C. at a pressure of 40-80 mbar in order to remove light compounds such as water and short chain hydrocarbons. In another embodiment, two evaporators are employed, the first evaporator (e.g. a thin-film evaporator) operating at 150-230° C. and 40-80 mbar, and the second evaporator operating at 300-390° C. and 0.01-15 mbar. In a further embodiment, three evaporators are employed, the first evaporator operating at 150-230° C. and 40-80 mbar, the second evaporator operating at 200-280° C. and approximately 2-3 mbar, and the third evaporator operating at 250-360° C. and approximately 0.3 mbar. These embodiments are particularly suited to the purification of crude tall oil. The residue of the first evaporator is fed to the second evaporator, and the distillate of the second evaporator is fed to the third evaporator. The use of an initial evaporation step enables boiling in the subsequent step to be performed in a controlled manner since low boiling compounds are removed in the first step.

Prior to hydroprocessing, the feedstock may be passed through one or more guard units together with hydrogen in order to remove hazardous substances such as metal residues, thereby protecting the hydroprocessing catalysts from poisoning and fouling. For this, the guard units can comprise an HDO and/or multifunctional catalyst arranged in one or more beds. These catalysts are as described above for the hydroprocessing step, the difference being that the catalysts used in the guard unit(s) typically have a lower activity; for instance, a NiMo catalyst used in a guard unit has a relatively low hydrogenation activity.

Guard units are typically separate from the hydroprocessing reactor(s). However, it is possible to include one or more guard beds upstream of the hydroprocessing catalyst bed(s) in the same unit (pressure vessel).

The hydroprocessed composition can be cooled and light gaseous compounds such as water, hydrogen, hydrogen sulfide, carbon monoxide and carbon dioxide removed from the composition. The removed gases can be passed through an amine scrubber in order to separate hydrogen sulfide and carbon dioxide from the remaining gases. Hydrogen can be separated and reused as quench gas in the hydroprocessing reactor.

The composition of the invention is isolated by fractionation of the hydroprocessed composition, preferably following the removal of gases as described above. This step makes use of the distillation properties discussed above in order to separate the composition of the invention from relatively light hydrocarbons such as those in the gasoline range. The composition is typically distilled within the temperature range of 150-360° C., preferably 160-350° C., more preferably 165-350° C.

The composition of the invention can be used as a pure biofuel or can be blended with another fuel. Particularly suitable examples of the other fuel are petroleum-derived diesel and kerosene. Fuel blends can contain the composition in various amounts. Preferably, the composition is contained in a fuel blend in an amount of 5-98 vol. %, more preferably 5-50 vol. % and most preferably 5-30 vol. % based on the volume of the blend.

EXAMPLES

Example 1

A hydrocarbon composition was produced by subjecting crude tall oil to a hydroprocessing treatment. The crude tall oil originated from tall oil soap obtained from chemical digestion of a mixture of northern softwood (pine and spruce) and birch. The crude tall oil contained 51 mass % of fatty acids, 26 mass % of resin acids and 23 mass % of neutral compounds.

The crude tall oil was purified by three-step evaporation to remove 4% of the oil as a light fraction and 6% of the oil as a heavy pitch fraction. The purified oil was fed into a pilot reactor system together with hydrogen. The pilot reactor system contained a guard unit having two catalyst beds arranged in series. The catalyst beds each contained Ni, Mo and W as active metals and $SiO_2$ and $Al_2O_3$ as support materials and metal scavengers. Hydrogen was mixed with the feed upstream of the guard unit.

From the guard unit, the composition was passed to a hydroprocessing reactor together with hydrogen. The hydroprocessing reactor comprised four monolayered catalyst beds through which the reaction mixture was passed in a series-wise manner. The compositions of the catalyst beds are detailed in Table 1 below. Hydrogen was also introduced between the catalyst beds.

TABLE 1

| Catalyst bed no. | NiW/zeolite/$Al_2O_3$ (mass %) | NiMo/$Al_2O_3$ (mass %) |
|---|---|---|
| 1 | 20 | 80 |
| 2 | 90 | 10 |
| 3 | 95 | 5 |
| 4 | 100 | 0 |

The hydroprocessing conditions are detailed in Table 2 below.

TABLE 2

| WHSV | 0.60 |
|---|---|
| $H_2$/CTO feed rate (Nl/l) | 1500 |
| Pressure (bar) | 90 |
| Temperature (° C.) | 370 |

The hydroprocessed composition was passed to a separator for the removal of water and light gases. The composition was then passed to a fractionator, where a fraction distilling in the temperature range of 150-370° C. (diesel fuel range) was collected. Table 3 below details the amounts of the various components of the distillate, as determined by GC-MS. Saturated compounds were separated from aromatic compounds by HPLC for analysis of the alkane and cycloalkane amounts.

TABLE 3

| Component | Amount (mass %) |
|---|---|
| $C_{8-30}$ linear alkanes | 23.1 |
| $C_{9-23}$ linear alkanes | 23.0 |
| $C_{9-20}$ linear alkanes | 22.8 |
| $C_{15-18}$ linear alkanes | 17.4 |
| $C_{8-30}$ branched alkanes | 51.1 |
| $C_{8-30}$ linear alkanes + $C_{8-30}$ branched alkanes | 74.2 |
| $C_{8-30}$ cycloalkanes | 20.3 |
| $C_{8-30}$ linear alkanes + $C_{8-30}$ branched alkanes + $C_{8-30}$ cycloalkanes | 94.5 |
| $C_{7-20}$ aromatic hydrocarbons | 5.5 |
| $C_{7-20}$ monoaromatic hydrocarbons | 5.1 |
| $C_{8-30}$ linear alkanes + $C_{8-30}$ branched alkanes + $C_{8-30}$ cycloalkanes + $C_{7-20}$ aromatic hydrocarbons | 100 |

The density of the composition was 808.1 kg/m³ when measured at 15° C. using the method of EN ISO 12185.

Figure 2:
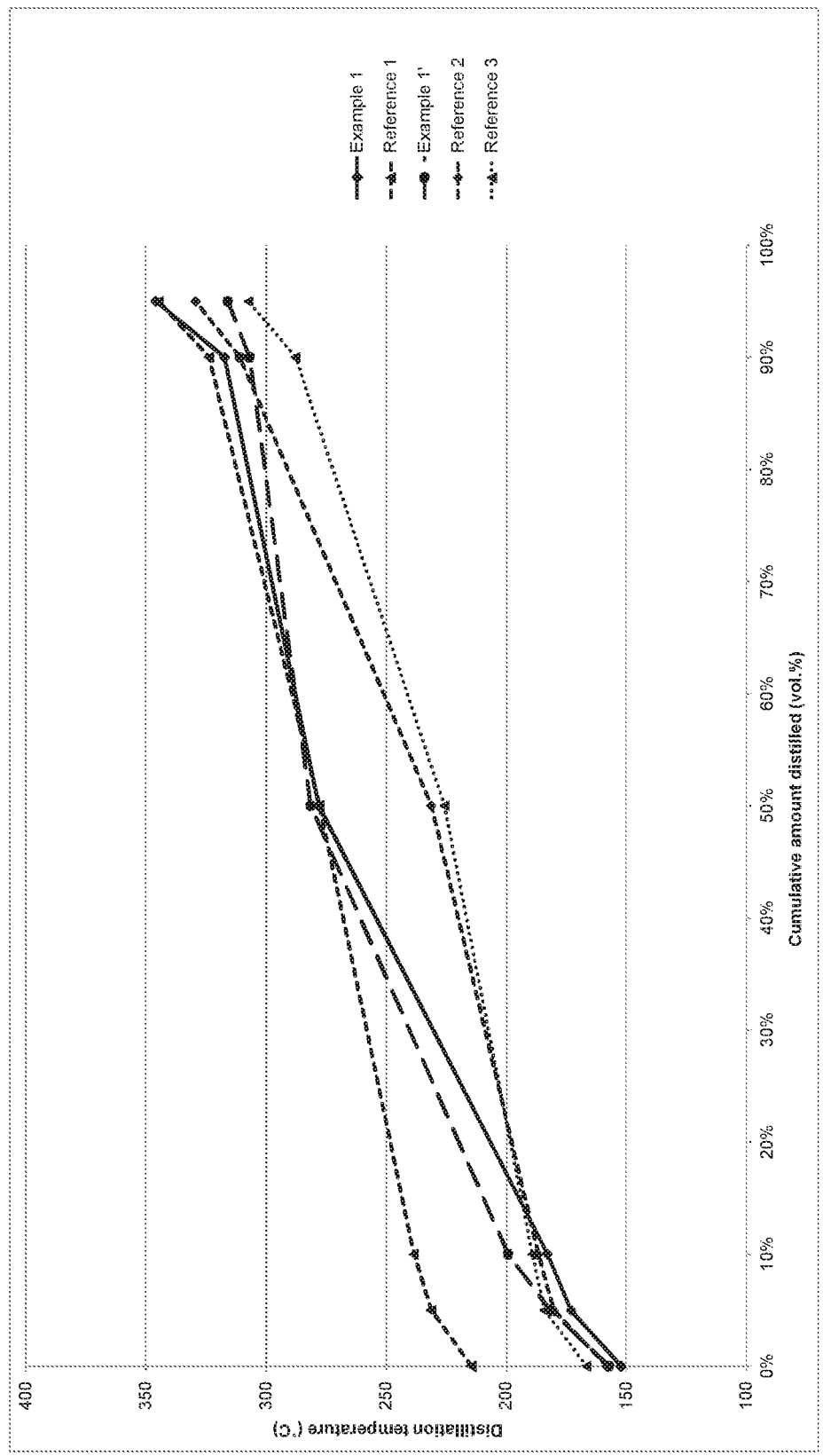
FIG. 2: Graph displaying distillation data for compositions of the present invention and reference compositions conforming to the EN 590 Standard.

The distillation properties of the composition are illustrated in FIG. 2, wherein the 0% temperature is the initial boiling point. FIG. 2 also illustrates the distillation properties of three reference compositions, which are all petrodiesel fuels conforming to the EN 590 Standard. Reference composition 1 is European Emission Certification Fuel CEC RF-06-03. Reference compositions 2 and 3 are both winter quality petrodiesel fuels. It is evident that, unlike conventional biodiesel, the composition of Example 1 has similar distillation properties to standard petrodiesel fuels.

95 vol. % of the composition of the invention was distilled at temperatures up to 345° C.

FIG. 2 additionally includes the distillation curve of another, very similar renewable diesel composition according to the present invention (Example 1'), which was obtained from the same hydroprocessed composition. 95 vol. % of this composition was distilled between 164° C. and 316° C.

Example 2

A second hydrocarbon composition was isolated from the hydroprocessed composition of Example 1 by subjecting the composition to distillation and collecting the components distilling in the temperature range of 170-300° C. The composition of the collected distillate is detailed in Table 4 below.

TABLE 4

| Component | Amount (mass %) |
|---|---|
| $C_{8-30}$ linear alkanes | 34.3 |
| $C_{9-23}$ linear alkanes | 33.3 |
| $C_{9-20}$ linear alkanes | 32.4 |
| $C_{15-18}$ linear alkanes | 23.9 |
| $C_{8-30}$ branched alkanes | 39.9 |
| $C_{8-30}$ linear alkanes + $C_{8-30}$ branched alkanes | 74.1 |
| $C_{8-30}$ cycloalkanes | 14.4 |
| $C_{8-30}$ linear alkanes + $C_{8-30}$ branched alkanes + $C_{8-30}$ cycloalkanes | 87.8 |
| $C_{7-20}$ aromatic hydrocarbons | 11.2 |
| $C_{7-20}$ monoaromatic hydrocarbons | 10.3 |
| $C_{8-30}$ linear alkanes + $C_{8-30}$ branched alkanes + $C_{8-30}$ cycloalkanes + $C_{7-20}$ aromatic hydrocarbons | 99.7 |

This composition is suitable for use as a component of aviation fuel.

The invention claimed is:

1. A composition comprising
10-40 mass % of $C_{8-30}$ linear alkanes,
up to 20 mass % of $C_{7-20}$ aromatic hydrocarbons, at least 90 mass % of which are monoaromatic, and no more than 1 mass % in total of oxygen-containing compounds;
wherein the total amount of $C_{8-30}$ alkanes in the composition is 50-95 mass %, and the total amount of $C_{8-30}$ alkanes, $C_{7-20}$ aromatic hydrocarbons and $C_{8-30}$ cycloalkanes is at least 95 mass %;
wherein the composition comprises 45-90 mass % in total of $C_{8-30}$ cycloalkanes and $C_{8-30}$ branched alkanes; and
wherein the amounts are based on the mass of the composition.

2. The composition according to claim 1, wherein the amount of $C_{8-30}$ linear alkanes is 20-40 mass %.

3. The composition according to claim 1, wherein the amount of $C_{7-20}$ aromatic hydrocarbons is 0.1-15 mass %.

4. The composition according to claim 1, which comprises 45-80 mass % in total of $C_{8-30}$ cycloalkanes and $C_{8-30}$ branched alkanes.

5. The composition according to claim 1, which comprises 10-30 mass % of $C_{8-30}$ cycloalkanes.

6. The composition according to claim 1, wherein the alkanes are $C_{9-23}$ alkanes.

7. The composition according to claim 1, wherein the aromatic hydrocarbons are $C_{8-19}$ aromatic hydrocarbons.

8. The composition according to claim 1, wherein the cycloalkanes are $C_{8-19}$ cycloalkanes.

9. The composition according to claim 1, which comprises no more than 1 mass % of polyaromatic hydrocarbons.

10. The composition according to claim 1, which comprises no more than 2 mass % of alkenes.

11. The composition according to claim 1, which has a density of 795-830 kg/m$^3$, as measured at 15° C. by the method of the EN ISO 12185 Standard.

12. The composition according to claim 1, which has a lower heating value of 42.0-45.0 MJ/l, as measured using the method of the DIN 51900 Standard.

13. The composition according to claim 1, which has a cetane number of at least 55, as measured using the method of the EN ISO 5165 Standard.

14. A method of producing a composition as defined in claim 1 comprising the steps of:
  (i) hydroprocessing a biological feedstock using one or more catalysts; and
  (ii) fractionating the product of step (i) to obtain a composition of claim 1.

15. The method according to claim 14, wherein the biological feedstock comprises a vegetable oil and/or an animal fat.

16. The method according to claim 14, wherein the biological feedstock comprises at least 15 mass % of $C_{12-18}$ fatty acids, at least 5 mass % of resin acids and at least 10 mass % of neutral compounds based on the mass of the feedstock.

17. The method according to claim 14, wherein the hydroprocessing step is performed using one or more catalysts which each comprise one or more metals selected from Group VIA and Group VIII metals and one or more support materials selected from zeolite, alumina, zeolite-alumina, alumina-silica, alumina-silica-zeolite and activated carbon.

18. The method according to claim 17, wherein the metals are selected from Mo, W, Co, Ni, Pt and Pd.

19. The method according to claim 17, wherein the hydroprocessing step is performed using one or both of the following catalysts (i) and (ii), and optionally the following catalyst (iii):
  (i) a catalyst comprising MoO$_3$, one or both of CoO and NiO, and one or more support materials;
  (ii) a catalyst comprising NiW and one or more support materials;
  (iii) a catalyst comprising a Group VIII metal and/or a molecular sieve;
  wherein the support materials are selected from zeolite, alumina, zeolite-alumina, alumina-silica, alumina-silica-zeolite and activated carbon.

20. The method according to claim 19, wherein the hydroprocessing step is performed using one or more reactors which each comprise catalysts (i) and (ii).

21. The method according to claim 20, wherein the amount of catalyst (ii) relative to the total amount of catalysts (i) and (ii) increases continuously in the direction of flow of the biological feedstock in the reactor(s).

22. The method according to claim 19, wherein the hydroprocessing step is performed using two or more reactors, at least one reactor comprising catalyst (i) and at least one other reactor comprising catalyst (ii) and/or catalyst (iii).

23. A fuel blend comprising a composition as defined in claim 1.

24. The fuel blend according to claim 23, which contains the composition in an amount of 5-98 vol. % based on the volume of the blend.

25. The fuel blend according to claim 23, which further comprises a petroleum-derived fuel.

26. The fuel blend according to claim 25, wherein the petroleum-derived fuel is petrodiesel or kerosene.

\* \* \* \* \*